OXYGENATOR WITH HEAT EXCHANGER

Original Filed Aug. 8, 1963 2 Sheets-Sheet 1

INVENTOR.
RICHARD A. DeWALL
BY Moore, White & Bond
ATTORNEYS

OXYGENATOR WITH HEAT EXCHANGER

Original Filed Aug. 8, 1963 2 Sheets-Sheet 2

INVENTOR.
RICHARD A. DeWALL
BY Moore, White & Bond
ATTORNEYS

United States Patent Office

Re. 27,100
Reissued Mar. 30, 1971

27,100
OXYGENATOR WITH HEAT EXCHANGER

Richard A. De Wall, Dayton, Ohio, assignor to Bentley Laboratories, Inc., Santa Ana, Calif.

Original No. 3,256,883, dated June 21, 1966, Ser. No. 300,757, Aug. 8, 1963. Application for reissue June 20, 1968, Ser. No. 741,813
Int. Cl. A61m *1/03;* A61f *7/00*
U.S. Cl. 23—258.5 19 Claims

Matter enclosed in heavy brackets [ ] appears in the original patent but forms no part of this reissue specification; matter printed in italics indicates the additions made by reissue.

This invention relates to an oxygenator for use in an extracorporeal circulation system for temporarily assuming or assisting the functions of the heart and lungs in a human being or other animal during surgery or other treatment of the body. More particularly, this invention relates to a simple disposable oxygenator device of simple construction and manufacture in which the temperature of the blood may be regulated.

The use of so called "heart-lung machines" has now become almost commonplace. Many types and varieties of heart-lung machines and component parts of such extracorporeal circulation systems have been proposed and described and illustrated in general, technical, and patent literature. My own prior Patents No. 2,854,002 granted September 30, 1958, No. 2,972,349 granted February 21, 1961 and No. 2,981,253 granted April 25, 1961 are exemplary of oxygenator devices which have been proposed and used.

As the art has advanced, there has been increasing demand for better devices which are of simpler construction, easier to manufacture and less expensive, so that each oxygenator device may be used but once and then discarded. There is also demand for means to permit control over the temperature of the blood, either to maintain it at body temperature, or at some lower temperature, as may be desirable as in a particular situation. While prior disposable bag-type oxygenators have been produced and more cumbersome temperaature control means have been available, the present oxygenating device for the first time combines a number of desirable features and functions in a single disposable oxygenator unit of novel structure which lends itself to ease of manufacture.

The principal object of this invention, therefore, is to provide a relatively simple disposable two-dimensional envelope or bag-type oxygenator comprised in large part of thermoplastic resinous sheet material heat sealed together to form the functional component parts.

A further object of this invention is to provide such a disposable bag-type oxygenator provided with temperature control means formed integral therewith from thermoplastic resinous sheet material heat sealed together and bonded to the oxygenator.

Another object is to provide an oxygenator of variable capacity so that a single size of device may be used for all patients from infants to large adults.

Other objects of the invention will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

The invention is illustrated by the accompanying drawings in which the same numerals refer to corresponding parts and in which.

Figure 1:
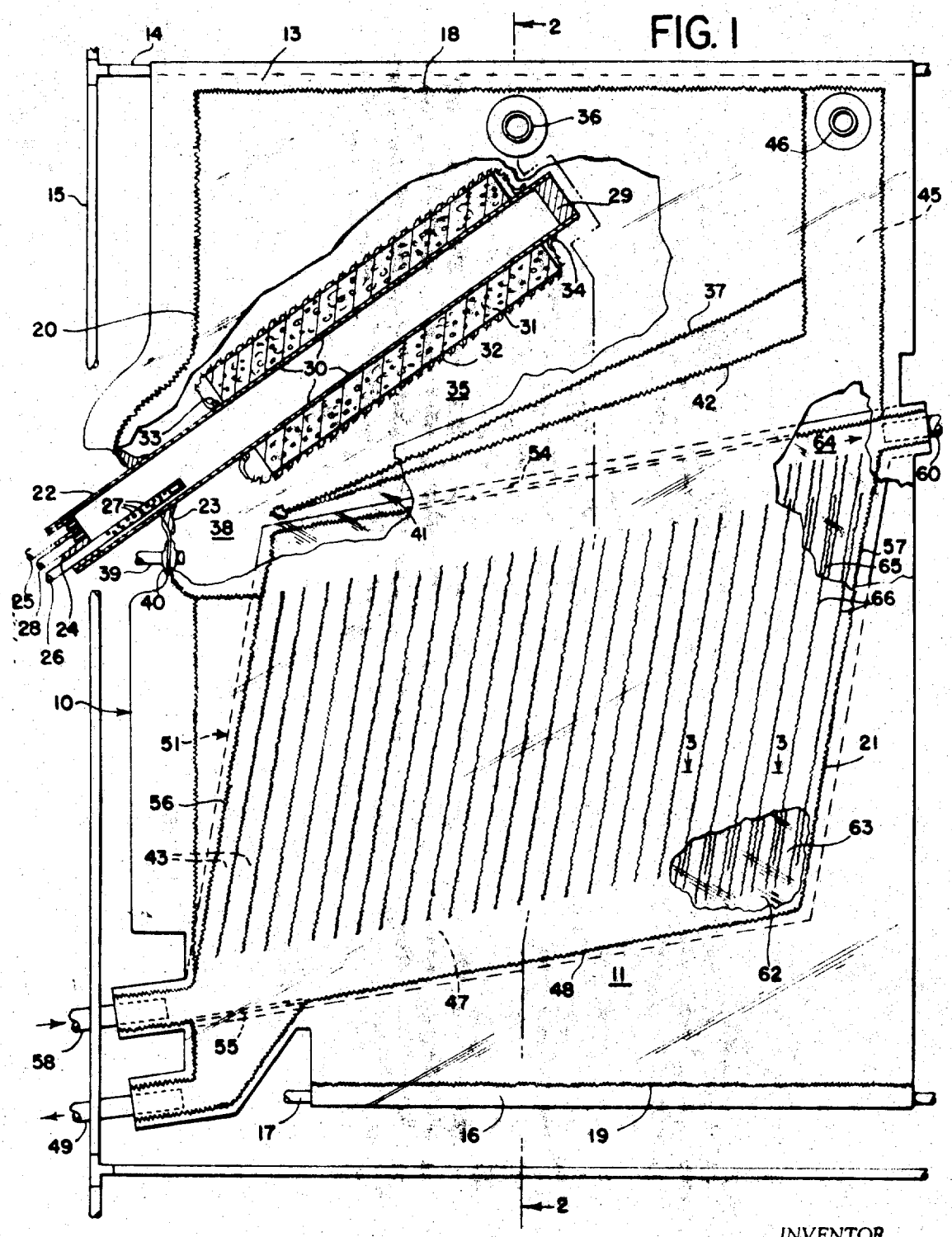
FIGURE 1 is a front elevation of the oxygenator according to the present invention, shown partly broken away to reveal structural details.

In the use of an extracorporeal circulation system, venous blood is withdrawn from the circulatory system of a living human being or other animal. This blood is pumped by mechanical means to the oxygenator device where it is mixed with pure oxygen. As the blood is admixed with oxygen, it tends to froth and foam and form bubbles. These gas bubbles must be removed from the blood before it is returned to the circulatory system of the patient in order to avoid possible dire results from air emboli. Accordingly, the oxygenated blood must first be defoamed in order to remove the larger and most obvious gas bubbles. Then, the blood is subjected to a further degassing or settling during which the blood separates differentially and the minute gas bubbles present in the blood rise to the surface of the blood and are dissipated. This degassed blood is then collected and pumped by mechanical means back to the patient.

One form of mechanical system is illustrated and described in my aforementioned Patent No. 2,854,002. The mechanical pumping system generally performs the function of the heart whereas the oxygenator performs generally the function of the lungs. The present invention is concerned with the latter.

Referring now to the drawings, the oxygenator device which is indicated generally at 10 is in the form of a large plastic bag including a front side wall 11 and a back side wall 12. The oxygenator 10 is provided with a top hem 13 through which a rod or bar type hanger 14 may be extended for the purpose of supporting the oxygenator in a frame 15 for suspension. In some instances a bottom hem 16 is also provided through which a rod or bar 17 may be passed in order to support the bottom end of the oxygenator in the frame.

The oxygenator side walls are formed from synthetic resinous sheet material which is impervious to passage of gases and liquids and which is thermoplastic in order to be heat sealable. The resinous material must be pure, inert and non-toxic in order to avoid contamination of blood passing through the oxygenator. It should also be flexible, odorless, tasteless and contain no leachable plasticizer or stabilizer. It must be of sufficient gauge so as to be strong enough to resist accidental puncturing or tearing. It must be sterilizable either by means of heat or by gas sterilization. Desirably it is transparent so that the functioning of the oxygenator may be observed.

Exemplary synthetic resinous materials which meet these requirements include polyethylene, polyvinyl chloride, trifluorochloroethylene and tetrafluoroethylene polymers, vinylidene chloride polymers and the like. Rigid resinous tubing used in parts of the oxygenator, as pointed out hereafter, may be formed from acrylic resins such as methyl methacrylate or the like resinous materials.

The side walls 11 and 12 are secured together adjacent the top and bottom and opposite side edges by heat seals in the form of narrow elongated fusion bonding areas 18, 19, 20 and 21, respectively. An elongated oxygen bubbler tube 22 is inserted into the oxygenator adjacent one edge. The bubbler tube is sealed into the bag by means of a esinous grommet 23 sealed to the sheet material of the walls and to the bubbler tube. The bubbler tube extends generally upwardly toward the top of the oxygenator, the precise angle being immaterial. Tube 22 is formed from rigid or semi-rigid resinous material having similar properties with respect to purity, non-toxicity, inertness, etc., as the side walls.

The lower end of tube 22 is fitted with a plug or stopper 24 provided with a plurality of ports. Into one of these ports is fitted a blood inlet tube 25. Another of the ports is fitted with an oxygen inlet tube 26. The oxygen is desirably introduced in the lowermost portion of the bubbler tube to avoid any accumulation or stagnant pool of blood in the bottom of the oxygen bubbler tube. The oxygen inlet tube is desirably in the form of a manifold tube which is closed at the end extending into the bubbler tube and is provided with a plurality of small perforations 27 for the purpose of breaking or subdividing the oxygen stream in order to insure thorough admixture between the oxygen and blood. The remaining port 28 is desirably made available for the purpose of introducing cardiotomy return blood or the like.

The upper end of bubbler tube 22 is desirably closed with a plug or stopper 29 in order to force the oxygenated blood out through a plurality of discharge ports 30 in the wall of tube 22 adjacent the upper end. The upper end of the bubbler tube thus functions as a manifold for distribution of oxygenated blood through the debubbler or defoaming means.

The defoaming means comprises a multi-cellular or spongelike mass surrounding the discharge ports of the bubbler tube through which the blood is forced to flow in a tortuous path. The anti-foam means shown is in the form of a sleeve 31 composed of silicone sponge material (Dow-Corning C–2–0033 or Q–3–0030) having anti-foaming properties. Alternatively, other rubber or resinous spongelike or fibrous matted material coated or impregnated with a non-toxic liquid silicone anti-foam material (Dow-Corning Anti-Foam A) may be used for this purpose. The anti-foam material is desirably held in place at the end of the bubbler tube by a sleeve 32 of fine mesh nylon filter cloth or the like held in place on the bubbler tube by means of a pair of collars 33 and 34.

Thus, blood and oxygen are introduced simultaneously under pressure into the lower end of the bubbler tube. The blood and oxygen are intermixed and ascend as a rising column of froth or foam. Since the rising column of blood and gas cannot escape through the end of the bubbler tube by virtue of stopper 29, the froth or foam is forced out through the ports 30 into contact with the anti-foam material contained in sleeve 31, and thence out through the fine filter 32.

The upper end of the bubbler tube including the defoaming means is contained in a relatively large chamber 35. This chamber 35 functions as part of the degassing means. In the bubbler tube, carbon dioxide contained in the venous blood is displaced by oxygen. This carbon dioxide plus excess oxygen removed from the blood by the defoaming means escapes into chamber 35 and is vented to the atmosphere through one or more vents 36 heat sealed into one of the walls of the oxygenator.

The bottom of chamber 35 is formed by a fusion bond 37 between the walls 11 and 12. This heat seal or fusion bonding area is disposed so that the bottom wall of chamber 35 slopes gently downwardly. The blood discharged through the defoaming means flows downwardly by gravity through the chamber 35 through a discharge port or passage 38 at the bottom of the chamber.

Blood containing residual minute gas bubbles is lighter than gas-free blood. The differential effect upon portions of blood of different density due to the forces of gravity causes the gas-containing blood to rise to the surface, from which the gas bubbles are dissipated and vented to the atmosphere.

An auxiliary port 39 is heat sealed into the edge seam of the oxygenator in the area of passage 38 by means of grommet 40 to provide means for the introduction of drugs, blood extenders, priming blood, and the like where needed or desired.

Completion of degassing of the blood and temperature control of the blood is accomplished in a multi-channel heat exchanger, disposed in the oxygenator below chamber 35 to receive the defoamed and partially degassed blood. Passage 38 from chamber 35 communicates with an upper blood distribution or manifold chamber 41, part of whose upper edge is defined by a heat seal 42. Chamber 41 is generally horizontal but is disposed at a slight angle inclined toward the discharge from the oxygenator. The bottom edge of chamber 41 communicates with a multiplicity of elongated, closely spaced, parallel blood flow channels or conduits 43 and 44. Channels or conduits 43 and 44 are disposed in a generally vertical direction but at a slight incline toward the discharge from the oxygenator.

The uppermost end of blood manifold chamber 41 communicates with a large vent chamber or passage 45, the upper end of which is fitted with one or more gas vents 46 heat sealed into the wall of the oxygenator. Gas escaping from blood within chamber 41 or channels or conduits 43 and 44 passes through the passage 45 and vent 46 to the atmosphere.

The bottom ends of channels or conduits 43 and 44 communicate into a collection chamber 47. The bottom wall of chamber 47 is formed by fusion bonding area 48 which is inclined downwardly for gravity flow of blood toward a discharge port 49 at the lowermost end of chamber 47 for discharge of the degassed blood. The blood discharge port 49 is in the form of a tube heat sealed into the seam of the oxygenator bag.

The temperature control or heat exchanger means as shown is in the form of a channeled internal water jacket which is heat sealed between the walls 11 and 12 of the oxygenator in the vicinity of the multiple channels or conduits 43 and 44 for the warming or cooling of the blood as it passes through those channels. The water jacket, indicated generally at 51, is formed by synthetic resinous sheet material having the same general properties as the oxygenator proper. It includes a front wall 52 and a back wall 53 generally heat sealed at the top, bottom and sides by means of relatively narrow elongated fusion bonding areas 54, 55, 56 and 57, respectively.

At one lower corner of the plastic envelope thus formed there is provided an inlet in the form of a tube 58 heat sealed into the seam. At the upper corner of the water jacket envelope on the opposite side is a water outlet or discharge in the form of a tube 60 heat sealed into the seam of the bag. Across the bottom of the water jacket is a water distribution or manifold chamber 62 which is elongated and generally horizontally disposed.

A series of elongated, parallel, closely spaced apart water channels 63 extend from the water distribution chamber 62. The upper ends of channels 63 communicate with a water collection and discharge chamber 64 which lies across the top of the water jacket and communicates with the water outlet 60.

Figure 3:
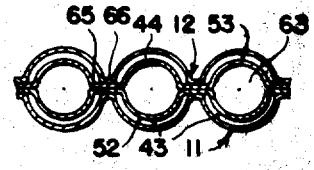
FIGURE 3 is an enlarged fragmentary section on the line 3—3 of FIGURE 1 and in the direction of the arrows showing details of construction of the temperature control portion of the oxygenator.
Figure 2:
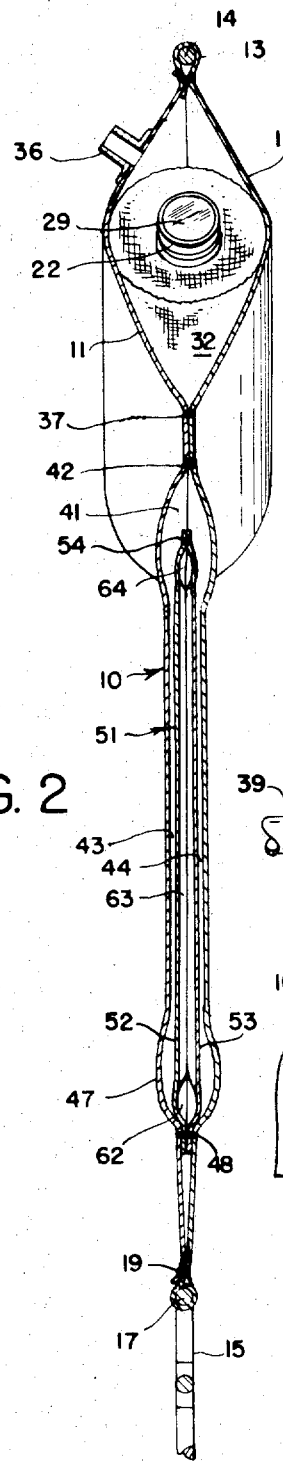
FIGURE 2 is an end elevation in section generally along the line 2—2 of FIGURE 1 and in the direction of the arrows.
Figure 4:
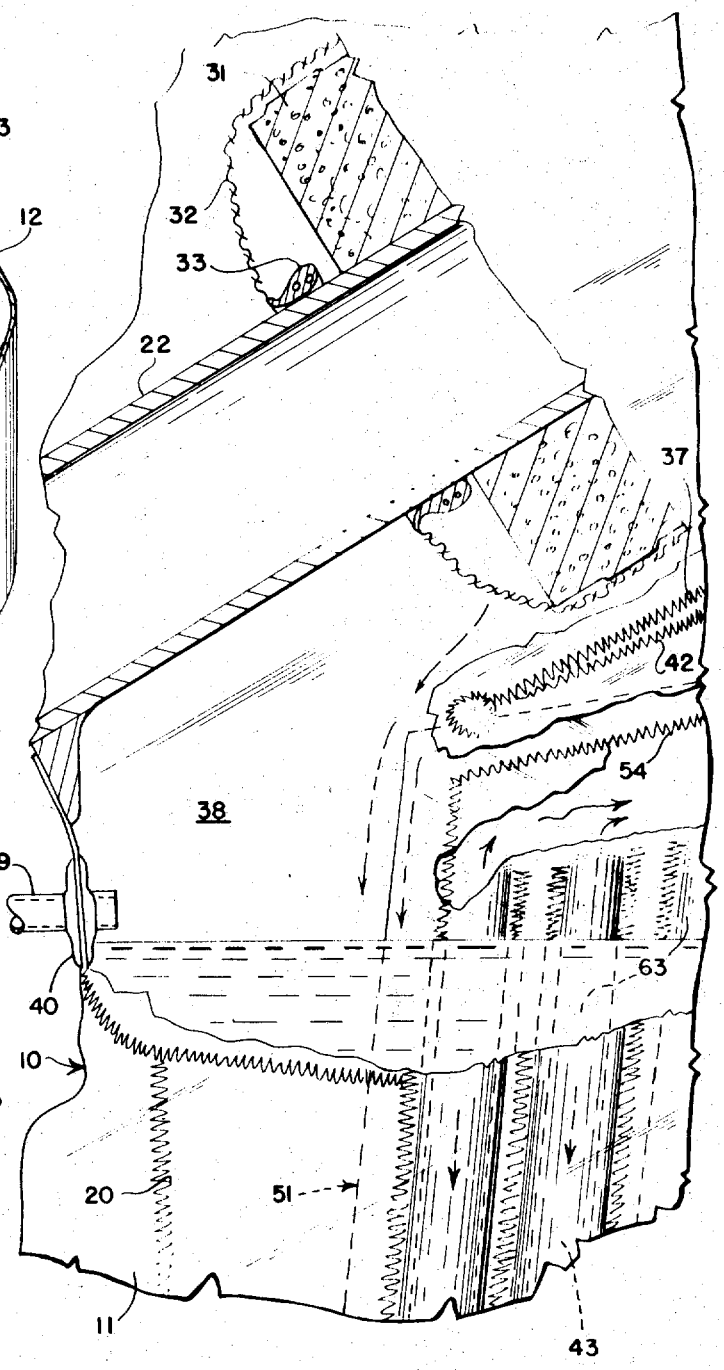
FIGURE 4 is an enlarged detail view, in section, further showing the construction of the oxygenator.

As best seen in FIGURE 3, the water channels 63 are formed between the walls 53 and 54 by means of relatively wide elongated, parallel, spaced apart fusion bonding areas 65 which secure the side walls 52 and 53 of the water jacket together. The blood channels or conduits 43 and 44 are defined by relatively narrower elongated, parallel, spaced apart fusion bonding areas 66 which overlie the fusion bonding areas 65 and secure the oxygenator walls 11 and 12 to the water jacket.

The result, as shown in FIGURE 3, is that the blood conduit 43 is formed between wall 11 of the oxygenator and wall 52 of the water jacket and blood conduit 44 is formed between wall 12 of the oxygenator and wall 53 of the water jacket. The relatively narrower heat seals delineating the blood channels overlying and centered on the heat seals delineating the water conduits insure that the blood conduits will remain open. There is no possibility that the walls of the blood conduits can remain collapsed against the walls of the water jacket channels.

Warming or cooling water or other temperature control liquid is pumped into the water inlet 58 at the bottom of the water jacket, forced up through the channels 63 and discharged from the water outlet 60 at the upper and opposite edge of the water jacket. Thus, the temperature control liquid flows in countercurrent heat exchanging flow with the blood in the surrounding blood channels 43 and 44 for effective temperature control of the blood.

Because of the slight inclination of the blood conduits from vertical, a laminar flow and differential separation of the blood results. Any residual gas escaping from the blood in its downward passage through the conduits, as a result of gravity separation, can escape along the inclined edge of the conduit for discharge into the blood distribution chamber 41 and vent passage 45.

In assembling the oxygenator, the water jacket is formed first by making the necessary heat seals in sheets 52 and 53. Then, this assembled structure is laid between sheets 11 and 12 and the remaining heat seals are made. The outer sheets may be sealed together without blocking or interfering with any of the chambers, channels or conduits formed between the heat seals of the water jacket.

The oxygenator according to the present invention is adapted for use for patients of all sizes from small infants to large adults. The capacity of the oxygenator is variable depending upon the number of blood channels which are utilized. For an infant patient, only the few channels to the left side of the oxygenator as illustrated might be needed, whereas, for a large adult, all of the channels are available. For this multi-purpose use, an oxygenator of size adaptable to a 30 by 36 inch frame is typical. A unit of this size then is capable of water flow through the water jacket of about 10 quarts per minute at average tap water pressure. A unit of the same size then has a flow capacity of up to about 4 quarts of blood per minute at a pressure head of approximately 2 feet of blood within the unit.

The unit is manufactured so as to avoid all pockets, voids or sharp edges in all areas of blood flow so as to prevent the accumulation of stagnant blood which tends to coagulate and may eventually break loose as hardened particles which would contaminate the system.

As used in this application, the expression "degassing" has reference to debubbling, or the liberation of excessive uncombined and undissolved gases in the blood. It does not refer to the removal of gases in chemical combination or in solution in the blood.

It is apparent that many modifications and variations of this invention as hereinbefore set forth may be made without departing from the spirit and scope thereof. The specific embodiments described are given by way of example only and the invention is limited only by the terms of the appended claims.

I claim:

1. A blood oxygenator comprising a pair of opposed plastic side wall members secured together in face-to-face abutting relation, an upper chamber formed by the confronting interior surfaces of said members, a bubbler tube inclined upwardly in said chamber from one side margin of said members, blood and oxygen inlets in the lower end of said tube, said tube having a closed upper end and discharge port means in the wall of the tube, a porous mass of deforming material surrounding said tube about said port means, a bonding line uniting said two members and forming a bottom in said chamber which slopes towards said one side margin, a temperature control chamber below said upper chamber formed by said interior surfaces of said members, a port in the lower end of said sloping bottom of said upper chamber for the gravity flow of blood from said upper chamber to the upper side of said temperature control chamber, a water jacket in said temperature control chamber having a water inlet and a water outlet, a bonding line uniting said two members and forming a bottom in said temperature control chamber which slopes toward said one side margin, a blood outlet at the lower end of said last sloping bottom, and gas vent means for said chambers.

2. A blood oxygenator comprising a pair of opposed plastic side wall members secured together in face-to-face abutting relation, an upper chamber formed by the confronting interior surfaces of said members, a straight bubbler tube inclined upwardly in said chamber from one side margin of said members, blood and oxygen inlets in the lower end of said tube, said tube having a closed upper end and discharge port means in the wall of the tube, a porous mass of defoamng material surrounding said tube about said port means and extending along a major portion of the length of said tube in said chamber, a cloth mesh filter surrounding said defoaming material, a bonding line uniting said two members and forming a bottom in said chamber which slopes toward said one side margin, a gas escape passageway extending upward along the opposite side margin of said members between said margin and said upper chamber, the upper end of said bonding line terminating at said passage so that the lower end of said passage communicates with the space below said bonding line, a gas escape vent in said upper chamber, a temperature control chamber below said upper chamber formed by said interior surfaces of said members, a port in the lower end of said sloping bottom of said upper chamber for the gravity flow of blood from said upper chamber to the upper side of said temperature control chamber, a water jacket in said temperature control chamber having a water inlet and a water outlet, a bonding line uniting said two members and forming a bottom in said temperature control chamber which slopes toward said one side margin, and a blood outlet connection at the lower end of said last sloping bottom.

3. A blood oxygenator comprising a unitary plastic casing containing an upper chamber and a lower chamber, means for suspending said casing in a vertical position, said casing having generally vertical opposite side edges, a straight bubbler tube inclined upwardly in said upper chamber from one sad side edges, blood and oxygen inlets in the lower end of said tube, said tube having a closed upper end and discharge port means in the wall of the tube, a porous mass of defoaming material surrounding said tube about said port means and extending along a major portion of the length of said tube in said chamber, a cloth filter surrounding said defoaming material, a bottom in said upper chamber sloping toward said one side edge, a vent passage in communication with said lower chamber extending upwardly along said opposite side edge between said opposite edge and said upper chamber, vent means for said upper chamber, a port in the lower end of said sloping bottom of said upper chamber for the gravity flow of blood from said upper chamber to the upper side of said lower chamber, a water jacket in said lower chamber having a water inlet and a water outlet, a bottom in said lower chamber sloping toward said one side edge, and a blood outlet at the lower end of said last sloping bottom.

4. In a bag-type blood oxygenator adapted to hang in a vertical position and having an envelope formed of a pair of plastic sheets sealed together on seal lines defining chambers and passages for the blood, a water jacket in said bag envelope comprising a pair of plastic sheets marginally sealed together in face-to-face relation to form an envelope, a plurality of straight and parallel seal lines slightly inclined from vertical uniting said water jacket sheets and formng water passages between said sheets extending between the top and bottom edges of the sheets, said parellel seal lines terminating short of said top and bottom marginal seals to provide a water inlet manifold chamber communicating with the lower ends of said water passages and a water outlet manifold chamber communicating with the upper ends of said water passages, water inlet and outlet connections for said manifold chambers, seal lines uniting the inner surfaces of said bag envelope to the outer surfaces of said water jacket envelope on said parallel, inclined seal lines of said water jacket to form a pair of blood passages on opposite sides of each water passage, a blood inlet manifold chamber in said bag envelope communicating with the upper ends of said blood passages, and a blood outlet manifold chamber in said bag envelope communicating with the lower ends of said blood passages.

5. A sterile, disposable, combined oxygenator and heat exchanger comprising: means to oxygenate blood with an oxygen containing gas; defoaming means to remove bubbles from the oxygenated blood and a heat exchanger to regulate the temperature of the blood, said heat exchanger having a plurality of channels for temperature regulating fluid; all of said means being enclosed in a sealed, substantially flattened, flexible walled container formed of heat sealable material, said container having inlet and outlet openings for the blood and similar openings for a temperature regulating fluid; an inlet opening for the oxygen containing gas, and an outlet opening for gas removed from the blood, said openings being marginally sealed to grommets connecting to each appropriate one of the aforesaid means, both said blood oxygenating means and said defoaming means being partially separated from said heat exchanger by transverse seals between mutually confronting inner surfaces of said flexible walled container to provide a passage between said defoaming means and said heat exchanger; and portions of said container walls being sealed to portions of said heat exchanger to define therewith concentric conduits to convey the oxygenated blood in contact with the requisite number of said heat exchanger channels and thence to said blood outlet openings.

6. A blood oxygenator comprising a pair of opposed plastic side wall members secured together in face-to-face abutting relation, an upper chamber formed by the confronting interior surfaces of said members, an upwardly extending bubbler tube mounted in said upper chamber, blood and oxygen inlets in the lower end of said tube, a plurality of discharge ports at different levels in the wall of said tube, a porous spongelike mass of defoaming material surrounding said tube about said ports, a bonding line uniting said two members and forming a sloping bottom for said chamber, a temperature control chamber below said upper chamber formed by said interior surfaces of said members, a discharge port in the lower end of said sloping bottom of said upper chamber communicating with the top of said temperature control chamber, a water jacket in said temperature control chamber having a water inlet and a water outlet, a bonding line uniting said two members and forming a sloping bottom for said temperature control chamber, a blood outlet at the lower end of said last sloping bottom, and gas escape vents in both of said chambers.

7. A blood oxygenator comprising a pair of opposed plastic side wall members secured together in face-to-face abutting relation, an upper chamber formed by the confronting interior surfaces of said members, a bubbler tube inclined upwardly in said chamber from one margin of said members, blood and oxygen inlets in the lower end of said tube, discharge ports at different levels in the wall of the tube, a porous spongelike mass of defoaming material surrounding said tube about said ports, a bonding line uniting said two members and forming a bottom in said chamber which slopes toward said one margin, a temperature control chamber below said upper chamber formed by said interior surfaces of said members, a discharge port in the lower end of said sloping bottom of said upper chamber communicating with the top of said temperature control chamber, a water jacket in said temperature control chamber having a water inlet and a water outlet, a bonding line uniting said two members and forming a bottom in said temperature control chamber which slopes toward said one margin, a blood outlet at the lower end of said last sloping bottom, a gas escape vent in said upper chamber, and a gas escape passageway extending upward from said temperature control chamber between said upper chamber and the opposite margin of said members.

8. A generally two-dimensional envelope or bag-type blood oxygenator comprising side walls of at least two sheets of synthetic resinous material which is inert, non-toxic, sterilizable and heat sealable secured together in face-to-face abutting relation; means at the top of said sheets to support the oxygenator by suspension; means enclosed by said sheets for successively oxygenating blood introduced into the oxygenator, de-foaming said oxygenated blood, de-gassing said de-foamed blood and collecting said de-gassed blood for return to a patient; said oxygenating means including an elongated tube extending generally upwardly toward the top of the oxygenator, a blood inlet to the lower end of said tube, an oxygen inlet to the same end of said tube, a blood outlet at the upper end of said tube; said de-foaming means being in direct fluid communication with said blood outlet and including a multicellular sponge-like mass having anti-foaming properties; said de-gassing means including a chamber formed between said sheets in direct fluid communication with said de-foaming means and having a diagonal downwardly extending bottom wall, a plurality of elongated channels formed between said sheets below said chamber in direct fluid communication with said chamber extending downwardly at an angle inclined slightly from vertical in closely spaced parallel relationship, and at least one gas escape vent in one of said sheets in the upper end of said chamber; said collecting means including a chamber formed between said sheets below said channels in direct fluid communications with the bottom ends of said channels and having a diagonal downwardly extending bottom wall and a discharge port in the bottom wall of said collecting chamber; means adjacent said de-gassing means for controlling the temperature of the blood, said temperature controlling means comprising a pair of sheets of synthetic resinous material which is inert, non-toxic, sterilizable and heat sealable secured together in face-to-face abutting relationship, said sheets being sealed adjacent their edges and enclosing a generally horizontally elongated chamber adjacent the bottom edges of said sheets, a temperature control liquid inlet to said lower chamber, a generally horizontal elongated chamber enclosed between said sheets adjacent the top edges thereof, a liquid outlet for said upper chamber, a plurality of generally vertical closely spaced elongated parallel channels formed between said sheets and extending between said lower and upper channels in direct fluid communication therewith, said channels being concentric with the channels of said blood de-gassing means but out of communication therewith.

9. An oxygenator according to claim 8 further characterized in that said temperature control means is enclosed between said sheets of material comprising the side walls of the oxygenator and said channels of the temperature control means are enclosed between the channels of the blood degassing means.

10. An oxygenator according to claim 9 further characterized in that the sheets of resinous material comprising said temperature control means are secured together by a plurality of relatively wide, closely spaced, elongated, parallel fusion bonding areas lying between the channels of said temperature control means, and the sheets of resinous material comprising the walls of said oxygenator are secured to the temperature control means in the area of the channels of the blood degassing means by a plurality of relatively narrower, closely spaced, elongated, parallel fusion bonding areas lying between the channels of both the temperature control means and the blood degassing means and overlying said first named fusion bonding areas, whereby the channels for flow of blood are wider than and extend around the channels for flow of temperature control liquid.

11. A generally two-dimensional envelope or bag-type blood oxygenator which comprises (A) a pair of opposed side walls of heat-sealable synthetic resinous sheet material, (B) means at the top of said side walls to support the oxygenator by suspension, (C) means enclosed between said side walls for successively (1) oxygenating blood introduced into the oxygenator, (2) defoaming the oxygenated blood, (3) degassing the defoamed blood, and (4) collecting the degassed blood for return to a patient, and simultaneously (5) controlling the temperature of said blood, (D) said oxygenating means including (1) a bubbler chamber, (2) means for simultaneously introducing blood and oxygen to said chamber, and (3) discharge means from said chamber, (E) said defoaming means including (1) a tortuous path flow means (a) connected to the discharge from said bubbling chamber, and (b) whose walls have anti-foaming properties, (F) said degassing means including (1) a chamber to receive defoamed blood and (2) means securing said opposed side walls together at intervals in face-to-face relationship so as to form a plurality of elongated channels connected to said chamber, (G) said collecting means including (1) a chamber to receive blood from said channels, (H) said temperature control means comprising (1) a water jacket having (a) a pair of opposed side walls of heat-sealable synthetic resinous sheet material, (b) a water inlet and water outlet, (c) means securing said last opposed side walls together at intervals in face-to-face relationship so as to form a plurality of elongated channels between said inlet and outlet, (d) said water jacket being disposed between said oxygenator side walls adjacent the channels of said degassing means.

12. An oxygenator according to claim 11 further characterized in that the perimeters of said oxygenator and the chambers and channels thereof are delineated by fusion bonding areas securing said sheets together.

13. An oxygenator according to claim 11 further characterized in that said temperature control means is enclosed between said sheets of material comprising the side walls of the oxygenator and said channels of the temperature control means are enclosed between the channels of the blood degassing means.

14. An oxygenator according to claim 13 further characterized in that the sheets of resinous material comprising said temperature control means are secured together by a plurality of relatively wide, closely spaced, elongated, parallel fusion bonding areas lying between the channels of said temperature control means, and the sheets of resinous material comprising the walls of said oxygenator are secured to the temperature control means in the area of the channels of the blood degassing means by a plurality of relatively narrower, closely spaced, elongated, parallel fusion bonding areas lying between the channels of both the temperature control means and the blood degassing means and overlying said first named fusion bonding areas, whereby the channels for flow of blood are wider than and extend around the channels for flow of temperature control liquid.

15. A generally two-dimensional envelope or bag-type blood oxygenator which comprises (A) a pair of side walls of at least two sheets of synthetic resinous material which is (1) inert, (2) non-toxic, (3) sterilizable, and (4) heat-sealable, (5) secured together in (a) face-to-face (b) abutting relation;

(B) hanger means at the top of said sheets to support the oxygenator by suspension;

(C) means enclosed between said side walls for successively (1) oxygenating blood introduced into the oxygenator, (2) defoaming the oxygenated blood, (3) degassing the defoamed blood, and (4) collecting said degassed blood for return to a patient, and simultaneously (5) controlling the temperature of said blood;

(D) said oxygenating means including (1) an elongated tube extending generally upwardly toward the top of the oxygenator, (2) a blood inlet to the lower end of said tube, (3) an oxygen inlet at the same end of said tube, and (4) a blood outlet at the upper end of said tube;

(E) said defoaming means (1) being in direct fluid communication with said blood outlet, and (2) including a multi-cellular spongelike mass (a) having anti-foaming properties;

(F) said degassing means including (1) a chamber (a) formed between said sheets, (b) in direct fluid communication with said defoaming means, (c) having a diagonal downwardly extending bottom wall, (2) a plurality of elongated channels (a) formed between said sheets, (b) below said chamber, (c) in direct fluid communication with said chamber, (d) extending downwardly (i) at an angle inclined slightly from vertical (e) in closely spaced, parallel relationship, and (3) at least one gas escape vent (a) in one of said sheets (b) in the upper end of said chamber;

(G) said collecting means including (1) a chamber (a) formed between said sheets, (b) below said channels, (c) in direct fluid communication with the bottom ends of said channels, (d) having a diagonal downwardly extending bottom wall, and (2) a discharge port in the bottom wall of said collecting chamber;

(H) said temperature control means comprising (1) a pair of sheets of synthetic resinous heat sealable material, (a) secured together in face-to-face abutting relation, ((b) sealed together adjacent their edges and enclosing (2) a generally horizontal elongated chamber adjacent the bottom edge of said sheets, (3) an inlet for introduction of temperature control liquid to said lower chamber,
(4) a generally horizontal elongated chamber adjacent the top edge of said sheets,
(5) an outlet for discharge of temperature control liquid from said upper chamber,
(6) a plurality of elongated channels
  (a) formed between said sheets
  (b) extending between said lower and upper chambers
    (i) in direct fluid communication therewith
  (c) in generally vertical, closely spaced parallel relationship,
  (d) extending parallel to and enclosed between the channels of said blood degassing means, but
    (i) out of communication therewith; and
(I) the perimeters of said oxygenator and the chambers and channels thereof being delineated by fusion bonding areas securing and heat-sealable sheets together.

16, An oxygenator according to claim 15 further characterized in that the sheets of resinous material comprising said temperature control means are secured together by a plurality of relatively wide, closely spaced, elongated, parallel fusion bonding areas lying between the channels of said temperature control means, and the sheets of resinous material comprising the walls of said oxygenator are secured to the temperature control means in the area of the channels of the blood degassing means by a plurality of relatively narrower, closely spaced, elongated, parallel fusion bonding areas lying between the channels of both the temperature control means and the blood degassing means and overlying said first named fusion bonding areas, whereby the channels for flow of blood are wider than and extend around the channels for flow of temperature control liquid.

*17. A blood oxygenator comprising a pair of opposed plastic side wall members secured together in face-to-face abutting relation, an upper chamber formed by the confronting interior surfaces of said members, a bubbler tube inclined upwardly in said chamber from one side margin of said members, said bubbler tube having discharge port means therein and being provided with blood and oxygen inlets in the lower end of said bubbler tube, a porous mass of defoaming material surrounding said tube about said port means, said upper chamber being provided with a downwardly sloping bottom below said bubbler tube for receiving the gravity flow of blood from said bubbler tube, a temperature control chamber below said upper chamber formed by said interior surfaces of said members, a passageway adjacent the lower end of said downwardly sloping bottom to receive the gravity flow of blood from the downwardly sloping bottom of said upper chamber and to conduct the gravity flow of blood to the upper side of said temperature control chamber, a water jacket in said temperature control chamber having a water inlet and a water outlet, said temperature control chamber having a downwardly sloping bottom, a blood outlet at the lower end of said sloping bottom, and gas vent means for said chambers.*

*18. A blood oxygenator as specified in claim 17, in which the temperature control chamber includes a collection chamber beneath the water jacket, and the downwardly sloping bottom formed in the collection chamber.*

*19. A blood oxygenator comprising a pair of opposed plastic side wall members secured together in face-to-face abutting relation, an upper chamber formed by the confronting interior surfaces of said members, a bubbler tube inclined upwardly in said chamber from one side margin of said members, said bubbler tube having discharge port means therein and being provided with blood and oxygen inlets in the lower end of said bubbler tube, a porous mass of defoaming material surrounding said tube about said port means and extending along a major portion of the length of said bubbler tube in said chamber, a cloth mesh filter surrounding said defoaming material, said upper chamber being provided with a bottom below said bubbler tube which bottom slopes downwardly toward said one side margin for receiving the gravity flow of blood from said bubbler tube, a temperature control chamber below said upper chamber formed by said interior surfaces of said members, a passageway adjacent the lower end of said bottom to receive the gravity flow of blood from the bottom of said upper chamber and to conduct the gravity flow of blood to the upper side of said temperature control chamber, a water jacket in said temperature control chamber having a water inlet and a water outlet, said temperature control chamber having a downwardly sloping bottom beneath the water jacket which bottom slopes toward said one side margin, a blood outlet connection at the lower end of said sloping bottom and gas vent means for said chambers.*

References Cited

The following references, cited by the Examiner, are of record in the patented file of this patent or the original patent.

UNITED STATES PATENTS

| | | | |
|---|---|---|---|
| 2,934,067 | 4/1960 | Calvin | 23—258.5 |
| 2,979,310 | 4/1961 | Nicholson | 165—143 |
| 3,087,490 | 4/1963 | Broman | 23—258.5 |
| 3,103,928 | 9/1963 | Broman | 23—258.5 |

FOREIGN PATENTS 1,283,603 12/1961 France.

OTHER REFERENCES

Belio et al.: "High Output Bubble Oxygenator With Variable Oxygenating Chamber for Cardiac By-Pass," Surgery, vol. 47, No. 5, May 16, 1960, pp. 772–83.

Bencini et al.: "Preliminary Studies of the Sponge-Oxygenator," Surgery, vol. 42, No. 2, August 1957, pp. 342–46.

Shumway et al.: "A Mechanical Pump-Oxygenator for Successful Cardiopulmonary By-Pass," Surgery, vol. 40, No. 5, November 1956, pp. 831–39.

DALTON L. TRULUCK, Primary Examiner

U.S. Cl. X.R.

128—400